(12) United States Patent
Hayden

(10) Patent No.: US 10,150,993 B2
(45) Date of Patent: Dec. 11, 2018

(54) MACROMOLECULE POSITIONING BY ELECTRICAL POTENTIAL

(71) Applicant: IBIS BIOSCIENCES, INC., Carlsbad, CA (US)

(72) Inventor: Mark A. Hayden, Ingleside, IL (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 654 days.

(21) Appl. No.: 14/367,789

(22) PCT Filed: Dec. 21, 2012

(86) PCT No.: PCT/US2012/071340
§ 371 (c)(1),
(2) Date: Jun. 20, 2014

(87) PCT Pub. No.: WO2013/096819
PCT Pub. Date: Jun. 27, 2013

(65) Prior Publication Data
US 2014/0318965 A1    Oct. 30, 2014

Related U.S. Application Data

(60) Provisional application No. 61/579,518, filed on Dec. 22, 2011.

(51) Int. Cl.
*C12Q 1/6869* (2018.01)
*C12Q 1/6874* (2018.01)
(Continued)

(52) U.S. Cl.
CPC ........ *C12Q 1/6869* (2013.01); *B01L 3/50273* (2013.01); *C12Q 1/6874* (2013.01);
(Continued)

(58) Field of Classification Search
CPC .................. C12Q 1/6869; C12Q 1/6874; C12Q 2561/10; G01N 33/54373;
(Continued)

(56) References Cited

U.S. PATENT DOCUMENTS 5,695,934 A    12/1997  Brenner
5,714,330 A    2/1998   Brenner et al.
(Continued)

FOREIGN PATENT DOCUMENTS

WO    9601836 A1    1/1996
WO    0018957 A1    4/2000
(Continued)

OTHER PUBLICATIONS

Adessi C., et al., "Solid Phase DNA Amplification: Characterisation of Primer Attachment and Amplification Mechanisms," Nucleic Acids Research, 2000, vol. 28 (20), pp. E87.
(Continued)

*Primary Examiner* — Sally A Merkling
(74) *Attorney, Agent, or Firm* — Casimir Jones, S.C.; David Casimir

(57) ABSTRACT

Provided herein is technology relating to depositing and/or placing a macromolecule at a desired site for an assay and particularly, but not exclusively, to methods and systems for placing or guiding a macromolecule such as a protein, a nucleic acid, or a protein: nucleic acid complex to an assay site, such as near a nanopore, a nanowell, or a zero mode waveguide.

14 Claims, 1 Drawing Sheet

(51) Int. Cl.
  *B01L 3/00* (2006.01)
  *G01N 27/447* (2006.01)
(52) U.S. Cl.
  CPC .............................. *G01N 27/44791* (2013.01);
    *B01L 2400/0421* (2013.01); *B01L 2400/0424*
    (2013.01); *C12Q 2561/10* (2013.01); *G01N*
    *2550/00* (2013.01)
(58) Field of Classification Search
  CPC .......... G01N 27/44791; G01N 2550/00; B01L
    3/50273; B01L 2400/0424; B01L
    2400/0421
  See application file for complete search history.

(56) References Cited

U.S. PATENT DOCUMENTS

| | | | |
|---|---|---|---|
| 5,750,341 | A | 5/1998 | Macevicz |
| 5,912,148 | A | 6/1999 | Eggerding |
| 5,976,336 | A | 11/1999 | Dubrow et al. |
| 6,017,696 | A * | 1/2000 | Heller .................. B01J 19/0046 |
| | | | 257/E21.705 |
| 6,130,073 | A | 10/2000 | Eggerding |
| 6,210,891 | B1 | 4/2001 | Nyren et al. |
| 6,258,568 | B1 | 7/2001 | Nyren |
| 6,261,776 | B1 | 7/2001 | Pirrung et al. |
| 6,306,597 | B1 | 10/2001 | Macevicz |
| 6,432,360 | B1 | 8/2002 | Church |
| 6,485,944 | B1 | 11/2002 | Church et al. |
| 6,511,803 | B1 | 1/2003 | Church et al. |
| 6,787,308 | B2 | 9/2004 | Balasubramanian et al. |
| 6,818,395 | B1 | 11/2004 | Quake et al. |
| 6,833,246 | B2 | 12/2004 | Balasubramanian |
| 6,911,345 | B2 | 6/2005 | Quake et al. |
| 6,969,488 | B2 | 11/2005 | Bridgham et al. |
| 7,115,400 | B1 | 10/2006 | Adessi et al. |
| 7,169,560 | B2 | 1/2007 | Lapidus et al. |
| 7,170,050 | B2 | 1/2007 | Turner et al. |
| 7,282,337 | B1 | 10/2007 | Harris |
| 7,302,146 | B2 | 11/2007 | Turner et al. |
| 7,313,308 | B2 | 12/2007 | Turner et al. |
| 7,329,492 | B2 | 2/2008 | Hardin et al. |
| 7,476,503 | B2 | 1/2009 | Turner et al. |
| 7,482,120 | B2 | 1/2009 | Buzby et al. |
| 7,486,865 | B2 | 2/2009 | Foquet et al. |
| 7,501,245 | B2 | 3/2009 | Quake et al. |
| 7,907,800 | B2 | 3/2011 | Foquet et al. |
| 8,153,375 | B2 | 4/2012 | Travers et al. |
| 8,501,405 | B2 | 8/2013 | Korlach et al. |
| 2005/0130173 | A1 | 6/2005 | Leamon et al. |
| 2009/0026082 | A1 | 1/2009 | Rothberg et al. |
| 2009/0035777 | A1 | 2/2009 | Kokoris et al. |
| 2009/0127589 | A1 | 5/2009 | Rothberg et al. |
| 2009/0208957 | A1 * | 8/2009 | Korlach ............... C12Q 1/6874 |
| | | | 435/6.12 |
| 2010/0035254 | A1 | 2/2010 | Williams |
| 2010/0081143 | A1 | 4/2010 | Rank et al. |
| 2010/0137143 | A1 | 6/2010 | Rothberg et al. |
| 2010/0167299 | A1 | 7/2010 | Korlach |
| 2010/0188073 | A1 | 7/2010 | Rothberg et al. |
| 2010/0197507 | A1 | 8/2010 | Rothberg et al. |
| 2010/0301398 | A1 | 12/2010 | Rothberg et al. |
| 2010/0323912 | A1 | 12/2010 | Korlach et al. |
| 2012/0014837 | A1 * | 1/2012 | Fehr .................. B01L 3/502707 |
| | | | 422/82.11 |

FOREIGN PATENT DOCUMENTS

| | | |
|---|---|---|
| WO | 2006084132 A2 | 8/2006 |
| WO | 2011103497 A1 | 8/2011 |

OTHER PUBLICATIONS

Astier Y., et al., "Toward Single Molecule DNA Sequencing: Direct Identification of Ribonucleoside and Deoxyribonucleoside 5'-monophosphates by Using an Engineered Protein Nanopore Equipped with a Molecular Adapter," Journal of the American Chemical Society, 2006, vol. 128 (5), pp. 1705-1710.
Bennett S.T., et al., "Toward the 1,000 Dollars Human Genome," Pharmacogenomics, 2005, vol. 6 (4), pp. 373-382.
Birren B., et al., eds., Genome Analysis—A Laboratory Manual, vol. 1, Cold Spring Harbor Laboratory Press, 1997, Table of Contents.
Brenner S., et al., "Gene Expression Analysis by Massively Parallel Signature Sequencing (MPSS) on Microbead Arrays," Nature Biotechnology, 2000, vol. 18 (6), pp. 630-634.
Co-pending U.S. Appl. No. 11/671,956, filed Feb. 6, 2007.
Co-pending U.S. Appl. No. 11/781,166, filed Jul. 20, 2007.
Eid J., et al., "Real-time Dna Sequencing from Single Polymerase Molecules," Science, 2009, vol. 323 (5910), pp. 133-138.
Foquet M., et al., "Improved Fabrication of Zero-mode Waveguides for Single-molecule Detection," Journal of Applied Physics, 2008, vol. 103.
International Search Report and Written Opinion for Application No. PCT/US2012/071340, dated May 15, 2013, 14 pages.
Korlach J., et al., "Selective Aluminum Passivation for Targeted Immobilization of Single DNA Polymerase Molecules in Zero-Mode Waveguide Nanostructures," Proceedings of the National Academy of Sciences, 2008, vol. 105 (4), pp. 1176-1181.
Korlach J., et al., "Long, Processive Enzymatic Dna Synthesis Using 100% Dye-labeled Terminal Phosphate-linked Nucleotides," Nucleosides Nucleotides Nucleic Acids, 2008, vol. 27 (9), pp. 1072-1083.
Levene M.J., et al., "Zero-mode Waveguides for Single-molecule Analysis at High Concentrations," Science, 2003, vol. 299 (5607), pp. 682-686.
Lundquist P.M., et al., "Parallel Confocal Detection of Single Molecules in Real Time," Optics Letters, 2008, vol. 33 (9), pp. 1026-1028.
MacLean D., et al., "Application of 'next-generation' Sequencing Technologies to Microbial Genetics," Nature Reviews Microbiology, 2009, vol. 7 (4), pp. 287-296.
Margulies M., et al., "Genome Sequencing in Microfabricated High-Density Picolitre Reactors," Nature, 2005, vol. 437 (7057), pp. 376-380.
Mitra R.D., et al., "Fluorescent in Situ Sequencing on Polymerase Colonies," Analytical Biochemistry, 2003, vol. 320 (1), pp. 55-65.
Morozova O., et al., "Applications of Next-generation Sequencing Technologies in Functional Genomics," Genomics, 2008, vol. 92 (5), pp. 255-264.
Pennisi E., "Genomics. Semiconductors Inspire New Sequencing Technologies," Science, 2010, vol. 327 (5970), pp. 1190.
Shendure J., et al., "Accurate Multiplex Polony Sequencing of an Evolved Bacterial Genome," Science, 2005, vol. 309 (5741), pp. 1728-1732.
Voelkerding K.V., et al., "Next-Generation Sequencing: from Basic Research to Diagnostics," Clinical Chemistry, 2009, vol. 55 (4), pp. 641-658.

* cited by examiner

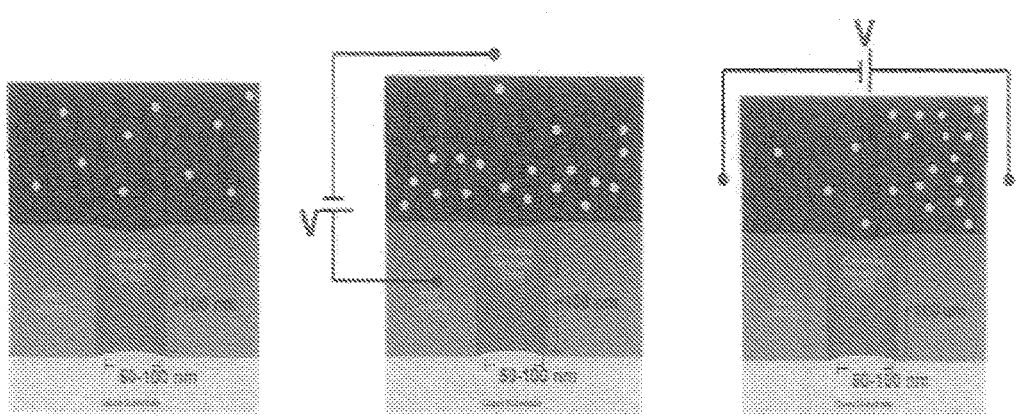

MACROMOLECULE POSITIONING BY ELECTRICAL POTENTIAL

FIELD OF INVENTION

Provided herein is technology relating to depositing and/or placing a macromolecule at a desired site for an assay and particularly, but not exclusively, to methods and systems for placing or guiding a macromolecule such as a protein, a nucleic acid, or a protein:nucleic acid complex to an assay site, such as near a nanopore, a nanowell, or a zero mode waveguide.

BACKGROUND

The massive parallelization of biological assays and realization of single-molecule resolution have yielded profound advances in the ways that biological systems are characterized and monitored and the way in which biological disorders are treated. Assays are able to interrogate thousands of individual molecules simultaneously, often in real time. In particular, the combination of solid state electronics technologies to biological research applications has provided a number of important advances including, e.g., molecular array technology, i.e., DNA arrays (see, e.g., U.S. Pat. No. 6,261,776), microfluidic chip technologies (see e.g., U.S. Pat. No. 5,976,336), chemically sensitive field effect transistors (ChemFETs), and other valuable sensor technologies.

These biochemical and medical assays often rely on the positioning of individual assay components on a molecular scale. Thousands of nanoscale assays are often patterned on a substrate for macro-manipulation, analysis, and data recording. Accordingly, new tools are needed to arrange and construct assay components with accuracy and precision at a molecular resolution.

Zero Mode Waveguides

In some assays, molecules are confined in a series, array, or other arrangement of small holes, pores, or wells, for example, a zero mode waveguide (ZMW). ZMW arrays have been applied to a range of biochemical analyses and have found particular usefulness for genetic analysis. ZMWs typically comprise a nanoscale core, well, or opening disposed in an opaque cladding layer that is disposed upon a transparent substrate, e.g., a circular hole in an aluminum cladding film deposited on a clear silica substrate. J. Korlach et al., Selective aluminum passivation for targeted immobilization of single DNA polymerase molecules in zero-mode waveguide nanostructures. 105 *PNAS* 1176-81 (2008). A typical ZMW hole is ~70 nm in diameter and ~100 nm in depth. ZMW technology allows the sensitive analysis of single molecules because, as light travels through a small aperture, the optical field decays exponentially inside the chamber. That is, due to the narrow dimensions of the well, electromagnetic radiation that is of a frequency above a particular cut-off frequency will be prevented from propagating all the way through the core. Notwithstanding the foregoing, the radiation will penetrate a limited distance into the core, providing a very small illuminated volume within the core. By illuminating a very small volume, one can potentially interrogate very small quantities of reagents, including, e.g., a single molecule and single molecule reactions. The observation volume within an illuminated ZMW is ~20 zeptoliters ($20 \times 10^{-21}$ liters). Within this volume, the activity of DNA polymerase incorporating a single nucleotide can be readily detected.

By monitoring reactions at the single molecule level, one can precisely identify and/or monitor a given reaction. The technology is not limited in the types of single molecule interactions that can be observed (e.g., a non-limiting list is protein-protein, protein-DNA, DNA-DNA, DNA-RNA, RNA-RNA, protein-RNA, lipid-lipid, protein-lipid, enzyme-substrate, enzyme-intermediate, enzyme-product, enzyme-metabolite, enzyme-cofactor, enzyme-inhibitor, etc.). In particular, the technology is the basis for a particularly promising field of single molecule DNA sequencing that monitors the molecule-by-molecule (e.g., nucleotide-by-nucleotide) synthesis of a DNA strand in a template-dependent fashion by a single polymerase enzyme (e.g., Single Molecule Real Time (SMRT) DNA Sequencing as performed, e.g., by a Pacific Biosciences RS Sequencer (Pacific Biosciences, Menlo Park, Calif.)). See, e.g., U.S. Pat. Nos. 7,476,503; 7,486,865; 7,907,800; and 7,170,050; and U.S. patent application Ser. Nos. 12/553,478, 12/767,673; 12/814,075; 12/413,258; and 12/413,466, each incorporated herein by reference in its entirety for all purposes. See also, Eid, J. et al. 2009. "Real-time DNA sequencing from single polymerase molecules", 323 *Science:* 133-38 (2009); Korlach, J. et al. "Long, processive enzymatic DNA synthesis using 100% dye-labeled terminal phosphate-linked nucleotides", 27 *Nucleosides, Nucleotides & Nucleic Acids:* 1072-82 (2008); Lundquist, P. M. et al., "Parallel confocal detection of single molecules in real time", 33 *Optics Letters:* 1026-28 (2008); Korlach, J. et al., "Selective aluminum passivation for targeted immobilization of single dna polymerase molecules in zero-mode waveguide nanostructures", 105 *Proc Natl Acad Sci USA:* 1176-81 (2008); Foquet, M. et al., "Improved fabrication of zero-mode waveguides for single-molecule detection", 103 *Journal of Applied Physics* (2008); and Levene, M. J. et al. "Zero-mode waveguides for single-molecule analysis at high concentrations", 299 *Science:* 682-86 (2003), each incorporated herein by reference in its entirety for all purposes.

In conventional use, placing components in the wells of the ZMW relies on simple diffusion to deliver components (e.g., macromolecules such as DNA polymerase and/or DNA and/or DNA/DNA polymerase complexes) to the desired site (e.g., near the opening or to the bottom of the ZMW well) in the zero mode waveguides. As a result, a significant amount of the macromolecule (e.g., the DNA polymerase/DNA complex) needs to be added to the ZMWs to achieve a critical mass sufficient to promote the diffusion of the complexes to a site near the openings of the wells or into the bottoms of the wells. This process is not efficient: e.g., only a fraction of the complexes reaches the desired sites in the wells and incubation times (e.g., 4 hours) are required to position the assay components in the proper sites.

SUMMARY

Provided herein is technology for the transport, delivery, and/or positioning of assay components (e.g., a macromolecule such as a DNA, a DNA polymerase, a DNA/DNA polymerase complex, a protein, etc.) to a desired site for an assay (e.g., near the opening of a ZMW or to the bottom of a ZMW well). The technology provides compositions, methods, and systems using an electrical potential (e.g., an electric field) to enhance the speed at which assay components are positioned at a desired site for an assay. In addition, the technology provides for improvements in the mixing of assay components.

These exemplary embodiments are not intended to limit the technology. Indeed, it is intended to be understood that the technology is widely applicable to any instance in which a molecule is delivered, positioned, or placed at a site, or wherein mixing is required. Additional embodiments will be apparent to persons skilled in the relevant art based on the teachings contained herein.

Accordingly, provided herein is technology providing methods, compositions, and systems for moving a macromolecule relative to an assay component, the composition comprising an electrode to generate an electric field; and an assay component comprising a site within the electric field, wherein the electric field generates a force upon the macromolecule; and the force moves the macromolecule relative to the site. The technology finds use in positioning and/or providing molecules for an assay or reaction; accordingly, some embodiments provide that an assay is performed at the site. In some embodiments, a DNA sequencing occurs at the site. In some embodiments, the composition provided by the present technology further comprises a phospholinked nucleotide, e.g., as a component for sequencing a DNA. Embodiments of the technology find use in positioning and/or providing a molecule to a nanopore, nanowell, or other structure or feature of an assay component. In some embodiments, the assay component comprises a zero mode waveguide. In some embodiments, the assay component comprises a nanowell.

The technology relates to the positioning, placement, and or movement of a molecule using an electric field (e.g., an electric potential). In some embodiments, the electric field results from an alternating current and in some embodiments the electric field results from a direct current. In some embodiments, the electric field induces mixing within the assay component, e.g., by changing a characteristic (e.g., the direction, strength, duty cycle, etc.) of the field, for instance to change the velocity of a molecule in relation to its milieu. Embodiments of the technology increase a concentration of the macromolecule near the zero mode waveguide.

The technology finds use in the positioning, movement, and placement of molecules by an electric field. In some embodiments, the molecule is a macromolecule (e.g., a biological molecule), e.g., in some embodiments the macromolecule comprises a protein (e.g., a DNA polymerase) and in some embodiments the macromolecule comprises a DNA. In some embodiments, the technology provides a composition comprising an anchor to maintain the macromolecule at the site, e.g., after the electric field has moved the macromolecule into position. Accordingly, the technology provided herein finds use in embodiments comprising compositions for moving a macromolecule to a site of an assay component, the composition comprising a first electrode and a second electrode to generate an electric field; and an assay component comprising a site within the electric field, wherein the electric field generates a force on the macromolecule that moves the macromolecule to the site faster than diffusion moves the macromolecule to the site; or mixes the macromolecule faster than diffusion mixes the macromolecule.

Also provided herein are embodiments of the technology that are methods for moving a macromolecule relative to an assay component, the method comprising generating an electric field; providing an assay component comprising a site within the electric field; and providing a macromolecule within the electric field, wherein the electric field generates a force upon the macromolecule; and the force moves the macromolecule relative to the site. In some embodiments, an assay is performed at the site and in some embodiments a DNA sequencing occurs at the site. Some embodiments further provide a phospholinked nucleotide, e.g., for DNA sequencing.

The methods find use in moving reagents and molecules, e.g., for assays occurring on an assay component. In some embodiments, the assay component comprises a zero mode waveguide. In some embodiments, the assay component comprises a nanowell.

Electric fields and/or electric potentials are provided in some embodiments of the methods by, e.g., an alternating current or a direct current. In some embodiments, the methods comprise providing an electric field to induce mixing within an assay component (e.g., by changing a characteristic of the electric field such as its direction, strength, or duty cycle). In some embodiments, the electric field increases a concentration of the macromolecule near the zero mode waveguide.

The technology finds use in the positioning, movement, and placement of molecules by an electric field. In some embodiments, the molecule is a macromolecule (e.g., a biological molecule), e.g., in some embodiments the macromolecule comprises a protein (e.g., a DNA polymerase) and in some embodiments the macromolecule comprises a DNA. In some embodiments, the technology provides anchoring the macromolecule at the site, e.g., after the electric field has moved the macromolecule into position. Accordingly, the technology provided herein finds use in embodiments comprising methods for moving a macromolecule to a site of an assay component, the method comprising providing a macromolecule to be positioned at a site of an assay component; and generating an electric field to produce a force on the macromolecule, wherein the force moves the macromolecule to the site faster than diffusion moves the macromolecule to the site. In addition, some embodiments provide a method wherein the force furthermore mixes the macromolecule faster than diffusion mixes the macromolecule.

An aspect of the technology provides embodiments of a system for moving a macromolecule relative to an assay component, the system comprising an electric field; an assay component comprising a site within the electric field; and a macromolecule within the electric field. In some embodiments, an assay is performed at the site and in some embodiments a DNA sequencing occurs at the site. Some embodiments further comprise a phospholinked nucleotide, e.g., for DNA sequencing. In some embodiments, the assay component comprises a zero mode waveguide and in some embodiments the assay component comprises a nanowell.

Embodiments of systems provided relate to positioning a molecule using an electric field. Thus, in some embodiments, the electric field results from an alternating current and in some embodiments the electric field results from a direct current. The electric field applies a force on the molecule such that the electric field, e.g., induces mixing within the assay component or increases a concentration of the macromolecule near the zero mode waveguide.

The technology finds use in the positioning, movement, and placement of molecules by an electric field. In some embodiments, the molecule is a macromolecule (e.g., a biological molecule), e.g., in some embodiments the macromolecule comprises a protein (e.g., a DNA polymerase) and in some embodiments the macromolecule comprises a DNA. Furthermore, some embodiments provide an anchor to maintain the macromolecule at the site. As such, provided herein are embodiments of technology that find use in a system for moving a macromolecule to a site of an assay component, the system comprising a first electrode and a second electrode to produce an electric field; an assay component comprising a site within the electric field; and a macromolecule to be positioned at the site, wherein the electric field generates a force on the macromolecule that moves the macromolecule to the site faster than diffusion moves the macromolecule to the site; or mixes the macromolecule faster than diffusion mixes the macromolecule. In some embodiments, the system is a system for sequencing a DNA, the system comprising an electrode to produce an electric field; an assay component comprising a site within the electric field; and a phospholinked nucleotide. The systems comprise in some embodiments a zero mode waveguide and in some embodiments an anchor at the site. Some embodiments further comprise a DNA polymerase within the electric field.

The technology is described in some instances as embodiments of a method of manufacturing an assay component comprising a macromolecule, the method comprising generating an electric field; providing an assay component comprising a site within the electric field; providing a macromolecule within the electric field; and moving the macromolecule to the site. In some embodiments, an assay is performed within the assay component and in some embodiments a DNA sequencing is performed within the assay component. The technology relates to moving molecules relative to an assay component, e.g., to position molecules on an assay component. In some embodiments the assay component comprises a zero mode waveguide. In some embodiments the assay component comprises a nanowell.

Aspects of the technology are associated with the movement of molecules by an electric field; accordingly, in some embodiments, the methods of manufacturing comprise producing an electric field by an alternating current and some embodiments comprise producing an electric filed by a direct current. The electric fields move molecules, e.g., in some embodiments inducing mixing within the assay component and in some embodiments increasing a concentration of the macromolecule near the zero mode waveguide.

The technology finds use in the positioning, movement, and placement of molecules by an electric field. In some embodiments, the molecule is a macromolecule (e.g., a biological molecule), e.g., in some embodiments the macromolecule comprises a protein (e.g., a DNA polymerase) and in some embodiments the macromolecule comprises a DNA. In some embodiments, the technology provides anchoring the macromolecule at the site, e.g., after the electric field has moved the macromolecule into position.

BRIEF DESCRIPTION OF THE DRAWINGS

These and other features, aspects, and advantages of the present technology will become better understood with regard to the following drawings:

FIG. 1 is a drawing showing the distribution of a macromolecule in an assay component using the conventional technology (left panel) and in an assay component using embodiments of the technology provided herein (middle and right panels).

DETAILED DESCRIPTION

Provided herein is technology for placing and/or depositing assay components (e.g., a macromolecule such as a DNA, DNA polymerase, DNA/DNA polymerase complex, a protein, etc.) at a desired site for an assay (e.g., near the opening of a ZMW well or to the bottom of a ZMW well). For example, the technology provides compositions, methods, and systems using an electric potential to move macromolecules to a desired location.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the term "site" is used to refer to a location in three dimensional space on a molecular scale that is of interest for the technology provided herein (e.g., where a measurement occurs and/or the position of a molecule). In some embodiments, the site is on a surface or on a substrate and in some embodiments the site is in a solution. For example, in some embodiments the site comprises a concentration or collection of molecules (biological molecules or other chemicals) that interact, for example in a biochemical (e.g., enzymatic) reaction (e.g., DNA synthesis). In some embodiments, an interaction of molecules occurs at the site and the interaction is measured, quantified, assessed, and/or otherwise evaluated. In some embodiments, the reactants and/or products consumed and/or produced at the site are measured, quantified, assessed, and/or otherwise evaluated. In some embodiments, the site is the position in space of a single molecule. In some embodiments, the site is the position of a single atom. In some embodiments, the site is at the bottom of a nanowell or zero mode waveguide where a macromolecular interaction or biochemical reaction is monitored. In some embodiments the site is at or near the opening of a nanowell, nanopore, or ZMW.

As used herein, a "phospholinked nucleotide" is a nucleotide having a label (e.g., a fluor or dye) attached to a phosphate (e.g., the terminal phosphate, e.g., the terminal phosphate of the NTP triphosphate chain). In some embodiments, upon incorporation of the labeled phospholinked nucleotide into the growing synthesized DNA molecule, the label (e.g., the flour or dye) is cleaved from the NTP.

As used herein, an "anchor" is a molecule or macromolecule that reversibly or irreversibly attaches, immobilizes, localizes, or associates a molecule, macromolecule, or atom to a surface or substrate.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule, but is intended to include other forms such as "portions", "fragments", "variants", and "mutants" as defined below. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid (for example, the range in size includes 4, 5, 6, 7, 8, 9, 10, or 11 . . . amino acids up to the entire amino acid sequence minus one amino acid).

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (e.g., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations. Examples of a protein domain include transmembrane domains and the glycosylation sites.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kbp on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA, or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, the sequence "5'-A-G-T-3'" is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

Embodiments of the Technology

When a solution is placed on the surface of a ZMW array, biological molecules of interest begin to diffuse into the wells at a rate dependent on the diffusion coefficient. Other factors influence diffusion rates, e.g., solution viscosity, temperature, and the size of the molecule. A medium-sized DNA (e.g., 1-10 kbp) traverses a distance x in one direction in a time t according to the following relationship:

$$t \approx x^2/D \quad (1)$$

where D is the diffusion coefficient in units of $cm^2/s$, t is the time in units of seconds, and x is the distance traveled in one direction by the DNA in units of cm. For example, a 4-kbp DNA with a diffusion coefficient of $D=1.94 \times 10^{-8}$ $cm^2/s$ will diffuse the following distances in the times indicated:

TABLE 1

| Distance | Diffusion time |
|---|---|
| 1 mm | 3 days |
| 100 μm | 43 minutes |
| 10 μm | 26 seconds |
| 1 μm | 260 milliseconds |

In contrast to diffusion, a DNA molecule under the influence of an electric field will migrate according to the following relationship:

$$v = \mu E \quad (2)$$

where v is velocity in units of cm/s, μ is an electrophoretic mobility constant, and E is the electric field strength in units of V/cm. According to this relation, the same 4-kbp DNA discussed above will have the following migration times under the influence of a 1 V/cm electric field:

TABLE 2

| Distance | Diffusion time | Electrical bias time (1 V/cm) |
|---|---|---|
| 1 mm | 3 days | 4.5 minutes |
| 100 μm | 43 minutes | 0.5 minutes |
| 10 μm | 26 seconds | 3 seconds |
| 1 μm | 260 milliseconds | 260 milliseconds |

Accordingly, for distances that are large on a molecular scale, the electrophoretic migration times are several orders of magnitude larger than the diffusion times. Faster times are possible by increasing the strength of the electric field beyond 1 V/cm (e.g., 2, 3, 4, 5, 10, 20, 50, 100, 1000, or more V/cm).

As such, in some embodiments, the technology comprises use of an external electric field for generating concentration gradients in a solution overlaying an assay component (e.g., a ZMW array). The electric field expedites the bulk transport of molecules from the solution to the surface of the assay component (e.g., the surface of the ZMW). Then, in some embodiments, passive diffusion subsequently moves the molecules farther, e.g., into the ZMW well. This technology reduces the incubation time associated with delivering macromolecules to the assay components, e.g., the openings and/or bottoms of ZMW wells.

In some embodiments, a ZMW array comprises an aluminum cladding and a silica base. In some embodiments, the aluminum comprises a passivation layer bonded to the exterior to decrease nonspecific binding; in some embodiments, the silica layer is derivatized to link the biological molecule of interest to the bottom of the well (e.g., to serve as an anchor).

The dimensions of a ZMW well are such that diffusion rates into the well are expected to be relatively fast once the molecule of interest arrives near the entrance of the ZMW well (e.g., near the top surface of the ZMW array). Embodiments of the technology reduce the lengthy time it takes for the molecules to move down to the ZMW surface or well, thus reducing incubation times.

In some embodiments, the electric field is applied horizontally (FIG. 1, right) and in some embodiments the electric field is applied vertically (FIG. 1, middle) to produce concentration gradients as desired (e.g., in the horizontal or vertical dimension). In some embodiments, the electrical potential is produced by a direct current (DC) and in some embodiments the electrical potential is produced by an alternating current (AC). In addition, in some embodiments the field is static, alternating, or rotating.

In some embodiments, the aluminum ZMW block is one electrode of the circuit. In some embodiments, an external electrode is positioned, e.g., at the site, e.g., either on top or on the bottom of the ZMW. It is contemplated as well that the electric field induces mixing in some embodiments. For example, by alternating the field at a specific frequency or mix of frequencies, the biological molecules are mixed periodically, at specific time intervals, or constantly. Producing concentration gradients according to the technology provided herein promotes the rapid entry of molecules into the wells instead of relying on diffusion.

Biological molecules are charged, e.g., carry an integral positive or negative charge (e.g., an ion), and/or are polar, e.g., carry an uneven distribution of electron density that results in a dipole moment. An electric field exerts a force on both types of molecules. A non-exhaustive list of the types of general classes of molecules that are charged and/or polar are nucleic acids, proteins, lipids, carbohydrates, cofactors, etc., and the components that compose these molecules such as nucleotides, amino acids, fatty acids, etc. Indeed, it is to be understood that the technology applies to any composition of matter (e.g., an atom, an ion, a cell, an organism) that carries a charge, is polar, or is otherwise affected by an electric field. In some embodiments, the molecules that are positioned according to the present technology are purified, isolated, semi-purified, or unpurified. In addition, in some embodiments, organisms are positioned (e.g., a bacterium, a nemotode, etc.). In some embodiments, the organisms are alive.

The charge and/or polarity of a molecule are influenced by various factors such as the ionic composition and pH of the solution comprising the molecule, the distribution of ions within the molecule's milieu, the activity of water and other components of the solution comprising the molecule, the type and number of the molecule's counter ions, the molecule's hydration shell, etc. Adjusting one or more of these parameters (e.g., pH) changes the ionization state of molecules such that they behave appropriately in an electric field. DNA and RNA are polyanions at physiological pH, therefore they are negatively charged in most pH-buffered solutions. Taq DNA polymerase has an isoelectric point ranging from 5-6, resulting in an overall net negative charge at pH 7. In general, nucleic acids and most DNA polymerases will be negatively charged in most molecular biology buffered solutions.

The technology finds use in DNA sequencing, e.g., single molecule sequencing. Single molecule sequencing systems, e.g., as developed by Pacific Biosciences are described in Voelkerding et al., 55 *Clinical Chem:* 641-58, 2009; MacLean et al., 7 *Nature Rev. Microbiol.:* 287-96; and in U.S. Pat. Nos. 7,170,050; 7,302,146; 7,313,308; and 7,476,503; all of which are herein incorporated by reference. This technology utilizes reaction wells 50-100 nm in diameter and encompassing a reaction volume of approximately 20 zeptoliters ($10^{-21}$ liters). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the technology finds use for the single molecule real time (SMRT) DNA sequencing methods using zero-mode waveguides (ZMWs) developed by Pacific Biosciences or similar methods. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospho-linked nucleotides, each type labeled with a different colored fluorophore, are then introduced into the reaction solution at high concentrations which promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

While particular embodiments are described herein in reference to particular DNA sequencing methods such as Single Molecule Real Time DNA sequencing as implemented by technologies developed by Pacific Biosciences, the technology of delivering a molecule or macromolecule (e.g., a polymerase or DNA) to a site finds use in other sequencing technologies.

In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics,* 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.,* 55:641-658, 2009; MacLean et al., *Nature Rev. Microbiol.,* 7:287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., *Clinical Chem.,* 55: 641-658, 2009; MacLean et al., *Nature Rev. Microbiol.,* 7.287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55.641-658, 2009; MacLean et al., *Nature Rev. Microbiol.*, 7:287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., *Clinical Chem.*, 55: 641-658, 2009; MacLean et al., *Nature Rev. Microbiol.*, 7:287-296; U.S. Pat. Nos. 7,169,560; 7,282, 337; 7,482,120; 7,501,245; 6,818,395; 6,911,345; 7,501, 245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.*, 55:641-58, 2009; U.S. Pat. No. 7,329,492; U.S. patent application Ser. Nos. 11/671,956; 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Other embodiments provide for the delivery of a molecule or macromolecule to a site for an assay. Assays for which the technology finds use are, e.g., an ELISA or other immunoassay, an array (e.g., of nucleic acids or proteins, e.g., antibodies), and other nucleic acid hybridization and/or protein detection assays.

Although the disclosure herein refers to certain illustrated embodiments, it is to be understood that these embodiments are presented by way of example and not by way of limitation. All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in molecular biology, genomics, biochemistry, medical science, materials science, or related fields are intended to be within the scope of the following claims.

EXAMPLE

Preparation of nucleic acid sequencing targets for a zero-mode waveguide (ZMW) consumable can be accomplished by pre-incubating the nucleic acid sample with a DNA polymerase in a buffered solution at a pH ranging from 6 to 9. It is anticipated that all necessary buffers and salts are included in the reagent mixture. An example buffer would be composed of 10-200 mM KCl, 10-500 mM Tris pH 8.0. After a specific incubation time to allow for template-polymerase binding, the sample mixture is placed in a ZMW apparatus. The ZMW disposable is composed of an aluminum cladding bottom portion containing the ZMW cells and an upper reservoir compartment containing the template/polymerase complex. In addition, an upper electrode is placed in the upper reservoir compartment and is electrically connected to the bottom aluminum cladding to form an electric circuit. A DC potential is applied to the circuit using a polarity that generates a positive surface charge on the bottom aluminum ZMW cladding. This results in a density gradient within the solution where the concentration of template/polymerase complex (macromolecular complex) will be higher near the aluminum ZMW surface. The voltage can range, for example, from 10 mV/cm to several volts/cm; the voltage time can range, for example, from 1 second to several minutes. The positive charge on the surface will influence the rate at which the template/polymerase complex migrates to the cell, in addition to entering a particular cell. For example, a potential bias of 1 V/cm for 5 minutes may be satisfactory to enhance the speed of entry by several orders of magnitude over simple diffusion.

It should be noted that metals other than aluminum may be used to make up the electrical circuit. Voltage strength and times would need to be empirically determined prior to the actual analysis of a sample. The sample is now ready for sequencing analysis.

We claim:

1. A method for moving a single macromolecule relative to an assay component, the method comprising:
   a) generating an electric field;
   b) providing an assay component comprising a zero mode wave guide comprising a nanoscale opening in a metal film on a transparent substrate and a site within the electric field; and
   c) providing a macromolecule within the electric field, wherein:
      1) the electric field generates a force upon the macromolecule; and
      2) the force moves the single macromolecule relative to the site; and
   wherein said electric field moves said single macromolecule to a surface of said zero mode wave guide and passive diffusion subsequently moves said single macromolecule into said zero mode wave guide.

2. The method of claim 1 wherein a DNA sequencing occurs at the site.

3. The method of claim 1 wherein the electric field increases a concentration of the macromolecule near the zero mode waveguide.

4. The method of claim 1 wherein the electric field induces mixing within the assay component.

5. The method of claim 1 wherein an assay is performed at the site.

6. The method of claim 1 wherein DNA sequencing occurs at the site.

7. The method of claim 1 further comprising providing a phospholinked nucleotide.

8. The method of claim 1 wherein the electric field results from an alternating current.

9. The method of claim 1 wherein the electric field results from a direct current.

10. The method of claim 1 wherein the macromolecule comprises a DNA.

11. The method of claim 1 further comprising anchoring the macromolecule at the site.

12. The method of claim 1 wherein the electrical field is applied vertically.

13. The method of claim 1 wherein the electrical field is applied horizontally.

14. The method of claim 1 wherein an aluminum ZMV block is an electrode of a circuit.

* * * * *